United States Patent
Sugawara

(10) Patent No.: US 11,315,361 B2
(45) Date of Patent: Apr. 26, 2022

(54) OCCUPANT STATE DETERMINING DEVICE, WARNING OUTPUT CONTROL DEVICE, AND OCCUPANT STATE DETERMINING METHOD

(71) Applicant: MITSUBISHI ELECTRIC CORPORATION, Tokyo (JP)

(72) Inventor: Hisashi Sugawara, Tokyo (JP)

(73) Assignee: MITSUBISHI ELECTRIC CORPORATION, Tokyo (JP)

( * ) Notice: Subject to any disclaimer, the term of this patent is extended or adjusted under 35 U.S.C. 154(b) by 0 days.

(21) Appl. No.: 16/982,132

(22) PCT Filed: Apr. 11, 2018

(86) PCT No.: PCT/JP2018/015255
§ 371 (c)(1),
(2) Date: Sep. 18, 2020

(87) PCT Pub. No.: WO2019/198179
PCT Pub. Date: Oct. 17, 2019

(65) Prior Publication Data
US 2021/0073522 A1    Mar. 11, 2021

(51) Int. Cl.
G06K 9/00 (2022.01)
G06V 40/16 (2022.01)
G06V 20/59 (2022.01)

(52) U.S. Cl.
CPC .......... G06V 40/174 (2022.01); G06V 20/597 (2022.01)

(58) Field of Classification Search
CPC .......... G06K 9/00302; G06K 9/00845; G08G 1/0962; G08G 1/09626; A61B 5/1114;
(Continued)

(56) References Cited

U.S. PATENT DOCUMENTS

2013/0142389 A1* 6/2013 Shimura ............ G06K 9/00617
382/103
2015/0092056 A1* 4/2015 Rau .................... G06K 9/00791
348/148
(Continued)

FOREIGN PATENT DOCUMENTS

JP     2005-13626 A    1/2005
JP     2008-99884 A    5/2008
(Continued)

OTHER PUBLICATIONS

Japanese Notice of Reasons for Refusal for Japanese Application No. 2020-512997, dated Mar. 30, 2021, with an English translation.
(Continued)

*Primary Examiner* — Ming Y Hon
(74) *Attorney, Agent, or Firm* — Birch, Stewart, Kolasch & Birch, LLP

(57) ABSTRACT

An occupant state determining device includes an image data acquiring unit for acquiring image data indicating an image captured by a camera used for image capturing in a vehicle cabin, an image recognition processing unit for performing image recognition processing on the captured image by using the image data, a moveless state determining unit for determining whether an occupant is in a moveless state by using a result of the image recognition processing, and an abnormal state determining unit for determining whether the occupant is in an abnormal state due to decrease in the degree of awakening by using a result of the determination by the moveless state determining unit, and the abnormal state determining unit determines that the occupant is in an abnormal state when the duration of the moveless state exceeds a reference time.

14 Claims, 11 Drawing Sheets

(58) Field of Classification Search
CPC ... A61B 5/1116; A61B 5/1121; A61B 5/1128; A61B 5/4809; A61B 5/163; A61B 5/168; A61B 5/18

See application file for complete search history.

(56) References Cited

U.S. PATENT DOCUMENTS

| | | | | |
|---|---|---|---|---|
| 2016/0103338 | A1* | 4/2016 | Hart | G02C 11/10 351/206 |
| 2016/0171319 | A1* | 6/2016 | Nagai | G06K 9/00604 382/103 |
| 2016/0180677 | A1* | 6/2016 | Reed | H04W 4/48 340/576 |
| 2017/0080947 | A1* | 3/2017 | Boos | A61B 3/14 |
| 2017/0169302 | A1* | 6/2017 | Omi | G06T 7/73 |
| 2017/0200449 | A1* | 7/2017 | Penilla | G10L 15/063 |
| 2017/0313319 | A1* | 11/2017 | Kishi | G05D 1/0248 |
| 2017/0316274 | A1* | 11/2017 | Noridomi | G06K 9/00845 |
| 2018/0162394 | A1* | 6/2018 | Kamiya | G06K 9/00805 |
| 2018/0285665 | A1* | 10/2018 | Paszkowicz | B60W 50/12 |
| 2019/0102638 | A1* | 4/2019 | Nanu | G06T 7/50 |
| 2019/0143993 | A1* | 5/2019 | Aoi | G06K 9/0061 340/439 |
| 2019/0147272 | A1* | 5/2019 | Yokota | B60W 50/14 340/576 |
| 2019/0336059 | A1* | 11/2019 | Takemoto | A61B 5/4809 |
| 2019/0367016 | A1* | 12/2019 | Brannstrom | G06T 7/70 |
| 2020/0290628 | A1* | 9/2020 | Pinoteau | B60W 40/09 |

FOREIGN PATENT DOCUMENTS

| | | |
|---|---|---|
| JP | 2010-97379 A | 4/2010 |
| JP | 2016-9258 A | 1/2016 |
| JP | 2017-49636 A | 3/2017 |
| JP | 2017-199279 A | 11/2017 |
| JP | 2017-219885 A | 12/2017 |

OTHER PUBLICATIONS

International Search Report, issued in PCT/JP2018/015255, dated Jun. 26, 2018.

* cited by examiner

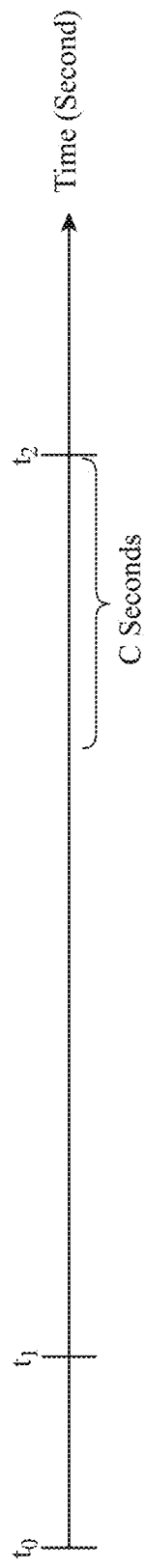

OCCUPANT STATE DETERMINING DEVICE, WARNING OUTPUT CONTROL DEVICE, AND OCCUPANT STATE DETERMINING METHOD

TECHNICAL FIELD

The present disclosure relates to an occupant state determining device, a warning output control device, and an occupant state determining method.

BACKGROUND ART

Conventionally, techniques of determining whether or not the driver is in an abnormal state due to decrease in the degree of awakening by using an image captured by a camera for image capturing in a vehicle cabin have been developed (refer to, for example, Patent Literatures 1 and 2). Hereafter, an abnormal state due to decrease in the degree of awakening may be simply referred to as an "abnormal state."

The technique described in Patent Literature 1 is one of performing image recognition processing on an image captured by a single camera, thereby detecting the eye opening degree of the driver. The technique described in Patent Literature 1 is one of determining whether or not the driver is in an abnormal state on the basis of the detected eye opening degree.

The technique described in Patent Literature 2 is one of determining whether or not the driver's head is included in an image captured by each of multiple cameras, thereby detecting a change in the driver's posture with respect to a forward inclination direction or a backward inclination direction. The technique described in Patent Literature 2 is one of determining whether or not the driver is in an abnormal state on the basis of the detected posture change.

CITATION LIST

Patent Literature

Patent Literature 1: JP 2008-99884 A
Patent Literature 2: JP 2017-49636 A

SUMMARY OF INVENTION

Technical Problem

Abnormal states due to decrease in the degree of awakening include a state in which a forward inclined posture occurs because of a loss of consciousness (referred to as a "forward inclined state" hereafter), a state in which a microsleep occurs with eyes open (referred to as a "microsleep state with eyes open" hereafter), a state in which a microsleep occurs with eyes closed (referred to as a "microsleep state with eyes closed" hereafter), and a state in which a backward inclined posture occurs because of a loss of consciousness (referred to as a "backward inclined state" hereafter).

Out of these abnormal states, a microsleep state with eyes closed is accompanied by a change in the eye opening degree, and a forward inclined state and a backward inclined state are accompanied by a posture change. Therefore, a microsleep state with eyes closed can be determined by the technique described in Patent Literature 1, and a forward inclined state and a backward inclined state can be determined by the technique described in Patent Literature 2. In contrast with this, in a microsleep state with eyes open, a change in the eye opening degree is small and a change in the posture is also small. Therefore, a problem is that a microsleep state with eyes open cannot be determined by the techniques described in Patent Literatures 1 and 2.

A further problem is that the technique described in Patent Literature 1 cannot determine an abnormal state in a state in which the eye opening degree is not detected normally (e.g., a state in which the driver is wearing sunglasses or the driver's eyes are hidden by the driver's forelock).

The present disclosure is made in order to solve the above-mentioned problems, and it is therefore an object of the present disclosure to provide an occupant state determining device, a warning output control device, and an occupant state determining method capable of determining an abnormal state including a microsleep state with eyes open, and determining an abnormal state regardless of whether or not an occupant is in a state in which the eye opening degree is not detected normally.

Solution to Problem

According to the present disclosure, an occupant state determining device includes processing circuitry to acquire image data indicating an image captured by a camera used for image capturing in a vehicle cabin, perform image recognition processing on the captured image by using the image data, determine whether an occupant is in a moveless state by using a result of the image recognition processing, and determine whether the occupant is in an abnormal state due to decrease in a degree of awakening by using a result of the determination, wherein the image recognition processing includes a process of detecting a face area in the captured image, when an amount of movement of the face area or an amount of change in a size of the face area is less than a reference quantity, the processing circuitry determines that the occupant is in the moveless state, and the processing circuitry determines that the occupant is in an abnormal state when a duration of the moveless state exceeds a reference time.

Advantageous Effects of Invention

According to the present disclosure, because the configuration is provided as above, an abnormal state including a microsleep state with eyes open can be determined, and an abnormal state can be determined regardless of whether or not the occupant is in a state in which the eye opening degree is not detected normally.

BRIEF DESCRIPTION OF DRAWINGS

FIG. 11A is an explanatory drawing showing an example of a predetermined time period associated with a histogram for comparison, FIG. 11B is an explanatory drawing showing an example of the x and y coordinates of the center of a face area associated with the histogram for comparison, and FIG. 11C is an explanatory drawing showing an example of the histogram for comparison;

DESCRIPTION OF EMBODIMENTS

Hereafter, in order to explain the present disclosure in greater detail, embodiments of the present disclosure will be described with reference to the accompanying drawings.

Embodiment 1

Figure 1:
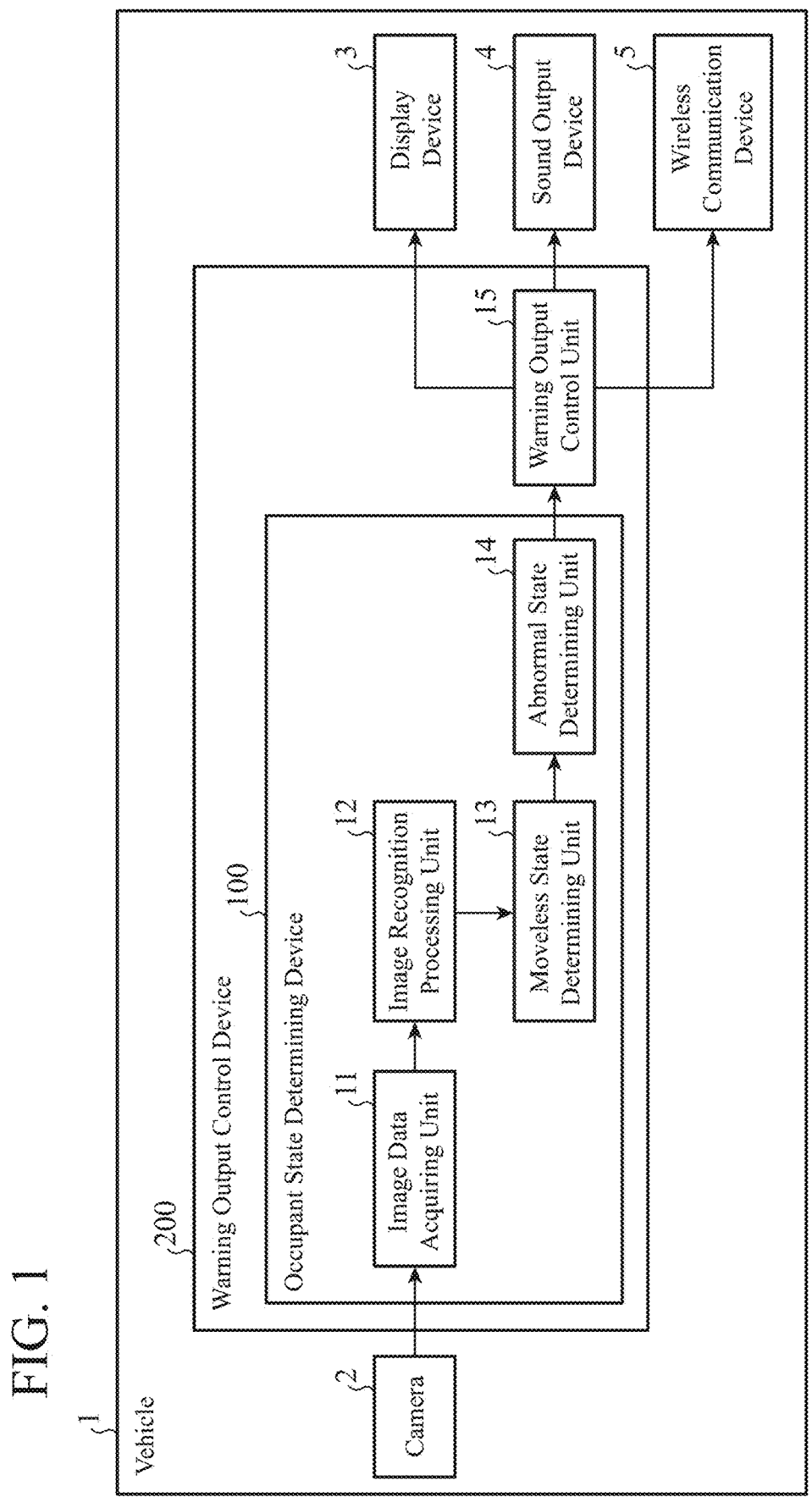
FIG. 1 is a block diagram showing a main part of a warning output control device according to Embodiment 1.
Figure 2:
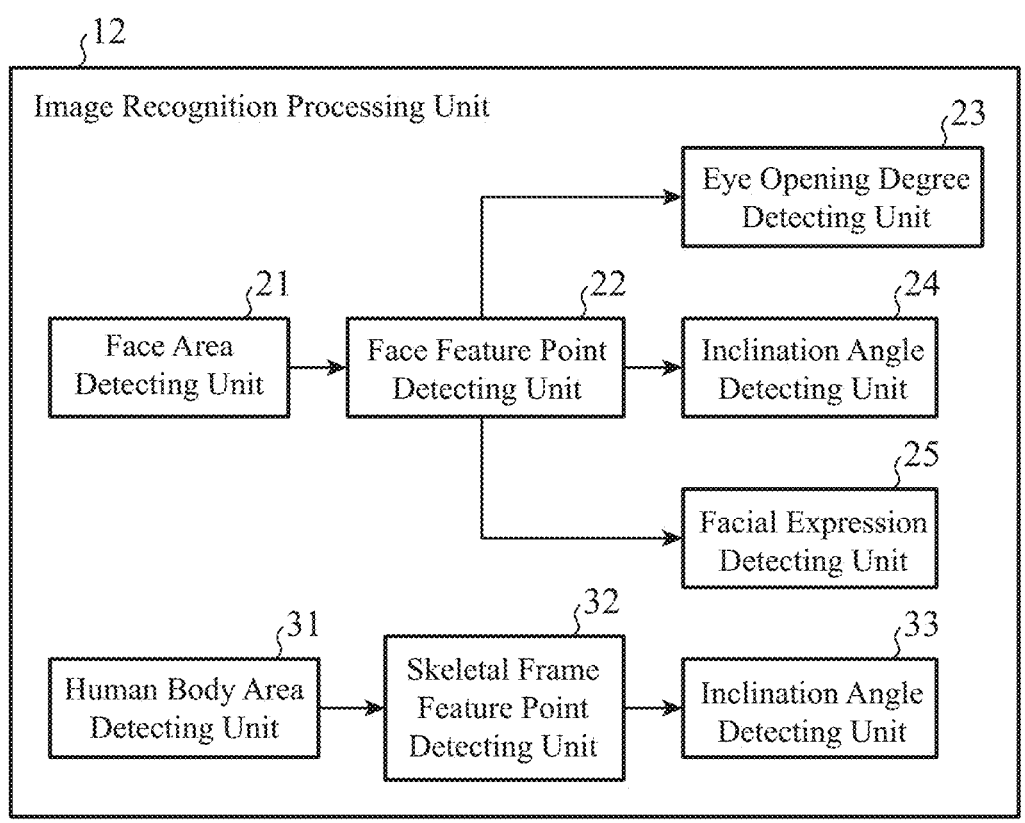
FIG. 2 is a block diagram showing a main part of an image recognition processing unit included in the warning output control device according to Embodiment 1.

FIG. 1 is a block diagram showing a main part of a warning output control device according to Embodiment 1. FIG. 2 is a block diagram showing a main part of an image recognition processing unit included in the warning output control device according to Embodiment 1. An occupant state determining device 100 of Embodiment 1 and the warning output control device 200 will be explained by reference to FIGS. 1 and 2.

A vehicle 1 has a camera 2 used for image capturing in the cabin thereof. The camera 2 is disposed in, for example, the center cluster of the vehicle 1. The camera 2 includes, for example, an infrared camera or a visible light camera.

An image data acquiring unit 11 acquires image data showing an image I captured by the camera 2 from the camera 2 at predetermined time intervals. The image data acquiring unit 11 outputs the acquired image data to an image recognition processing unit 12.

The image recognition processing unit 12 performs image recognition processing on the captured image I by using the image data outputted by the image data acquiring unit 11. The image recognition processing by the image recognition processing unit 12 includes, for example, below-mentioned processes by a face area detecting unit 21, a face feature point detecting unit 22, an eye opening degree detecting unit 23, an inclination angle detecting unit 24, a facial expression detecting unit 25, a human body area detecting unit 31, a skeletal frame feature point detecting unit 32, and an inclination angle detecting unit 33.

The face area detecting unit 21 detects an area (referred to as a "face area" hereafter) A1 in the captured image I, the area corresponding to the face of the driver of the vehicle 1. As a method of detecting the face area A1, well-known various methods can be used, and a detailed explanation of the method will be omitted hereafter. Hereafter, the driver of the vehicle 1 is simply referred to as the "driver."

The face feature point detecting unit 22 detects multiple feature points P1 in the face area A1, the multiple feature points P1 corresponding to several face parts of the driver. As a method of detecting feature points P1, well-known various methods can be used, and a detailed explanation of the method will be omitted hereafter.

Concretely, for example, the face feature point detecting unit 22 detects multiple feature points P1 corresponding to the driver's right eye, multiple feature points P1 corresponding to the driver's left eye, multiple feature points P1 corresponding to the driver's nose, and multiple feature points P1 corresponding to the driver's mouth. The multiple feature points P1 corresponding to the driver's right eye include, for example, a feature point P1 corresponding to the outer eye corner, a feature point P1 corresponding to the inner eye corner, a feature point P1 corresponding to the upper eyelid, and a feature point P1 corresponding to the lower eyelid. The multiple feature points P1 corresponding to the driver's left eye include, for example, a feature point P1 corresponding to the outer eye corner, a feature point P1 corresponding to the inner eye corner, a feature point P1 corresponding to the upper eyelid, and a feature point P1 corresponding to the lower eyelid. The multiple feature points P1 corresponding to the driver's nose include, for example, a feature point P1 corresponding to the nasal root, a feature point P1 corresponding to the nasal bridge, feature points P1 corresponding to the nasal wings, and a feature point P1 corresponding to the nasal tip. The multiple feature points P1 corresponding to the driver's mouth include, for example, a feature point P1 corresponding to the upper lip and a feature point P1 corresponding to the lower lip.

Figure 3A:
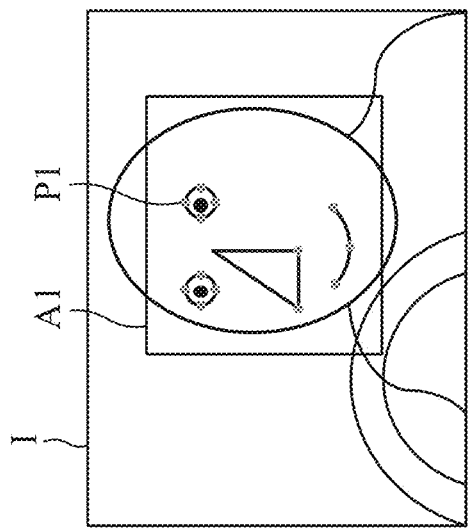
FIG. 3A is an explanatory drawing showing an example of a captured image.
Figure 3B:
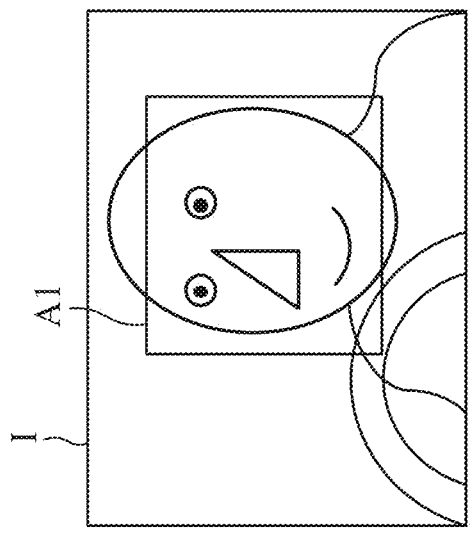
FIG. 3B is an explanatory drawing showing an example of a face area.
Figure 3C:
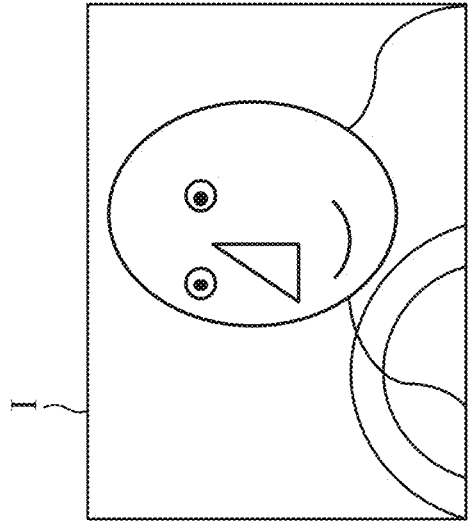
FIG. 3C is an explanatory drawing showing an example of multiple feature points.

FIG. 3A shows an example of the captured image I, FIG. 3B shows an example of the face area A1, and FIG. 3C shows an example of the multiple feature points P1. In the example shown in FIG. 3C, four feature points P1 corresponding to the driver's right eye, four feature points P1 corresponding to the driver's left eye, two feature points P1 corresponding to the driver's nose, and three feature points P1 corresponding to the driver's mouth are detected.

The eye opening degree detecting unit 23 detects the eye opening degree D of the driver by using multiple feature points P1 detected by the face feature point detecting unit 22 (more concretely, the multiple feature points P1 corresponding to the driver's right eye and the multiple feature points P1 corresponding to the driver's left eye). As a method of detecting the eye opening degree D, well-known various methods can be used, and the method is not limited to the following concrete example.

Concretely, for example, the eye opening degree detecting unit 23 calculates a current value of the distance between the feature point P1 corresponding to the upper eyelid and the feature point P1 corresponding to the lower eyelid (referred to as the "distance between the eyelids" hereafter). The eye opening degree detecting unit 23 calculates a reference value of the distance between the eyelids on the basis of the mode of the distances between the eyelids which are acquired within a predetermined time period. The eye opening degree detecting unit 23 calculates the eye opening degree D on the basis of the ratio of the current value to the reference value. More specifically, the unit of the eye opening degree D is percent.

The inclination angle detecting unit 24 detects inclination angles θ1 of the driver's head by using multiple feature points P1 detected by the face feature point detecting unit 22. As a method of detecting an inclination angle θ1, well-known various methods can be used, and a detailed explanation of the method will be omitted.

Inclination angles θ1 are detected with respect to, for example, a state in which the driver's face is directed toward the front of the vehicle 1, and the back of the driver's head is in contact with the headrest of the driver's seat (i.e., 0 degrees). For example, the inclination angle detecting unit 24 detects an inclination angle θ1 in a rotation direction around the driver's neck, an inclination angle θ1 with respect to a forward inclination direction or a backward inclination direction, and an inclination angle θ1 with respect to a rightward or leftward direction.

The facial expression detecting unit 25 detects the driver's facial expression by using multiple feature points P1 detected by the face feature point detecting unit 22. As a method of detecting a facial expression, well-known various methods can be used, and the method is not limited to the following concrete example.

Figure 4A:
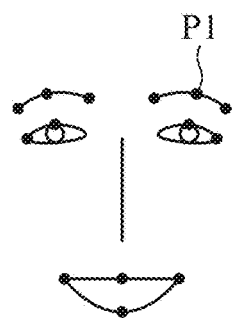
FIG. 4A is an explanatory drawing showing a positional relationship among multiple feature points which corresponds to a facial expression of happiness.
Figure 4B:
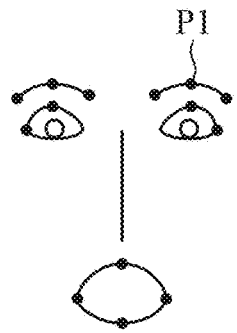
FIG. 4B is an explanatory drawing showing a positional relationship among multiple feature points which corresponds to a facial expression of surprise.
Figure 4C:
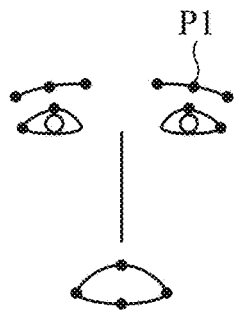
FIG. 4C is an explanatory drawing showing a positional relationship among multiple feature points which corresponds to a facial expression of fear.
Figure 4D:
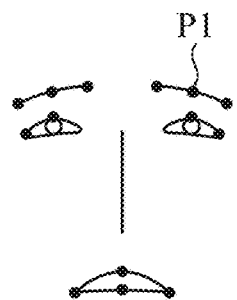
FIG. 4D is an explanatory drawing showing a positional relationship among multiple feature points which corresponds to a facial expression of sadness.
Figure 4E:
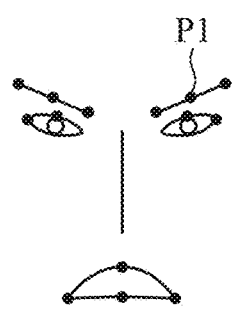
FIG. 4E is an explanatory drawing showing a positional relationship among multiple feature points which corresponds to a facial expression of anger.
Figure 4F:
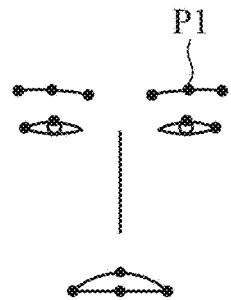
FIG. 4F is an explanatory drawing showing a positional relationship among multiple feature points which corresponds to a facial expression of disgust.

Concretely, for example, the facial expression detecting unit 25 detects the driver's facial expression on the basis of a positional relationship among three feature points P1 corresponding to the driver's right eyebrow, three feature points P1 corresponding to the driver's left eyebrow, two feature points P1 corresponding to the driver's right eye, two feature points P1 corresponding to the driver's left eye, and four feature points P1 corresponding to the driver's mouth, i.e., a positional relationship among the 14 feature points P1 in total. FIG. 4A shows an example of the positional relationship among the 14 feature points P1 which corresponds to a facial expression of happiness. FIG. 4B shows an example of the positional relationship among the 14 feature points P1 which corresponds to a facial expression of surprise. FIG. 4C shows an example of the positional relationship among the 14 feature points P1 which corresponds to a facial expression of fear. FIG. 4D shows an example of the positional relationship among the 14 feature points P1 which corresponds to a facial expression of sadness. FIG. 4E shows an example of the positional relationship among the 14 feature points P1 which corresponds to a facial expression of anger. FIG. 4F shows an example of the positional relationship among the 14 feature points P1 which corresponds to a facial expression of disgust.

The human body area detecting unit 31 detects an area A2 corresponding to the driver's face and body in the captured image I (referred to as a "human body area" hereafter). As a method of detecting the human body area A2, well-known various methods can be used, and a detailed explanation of the method will be omitted.

The skeletal frame feature point detecting unit 32 detects multiple feature points P2 in the human body area A2 which are used for the generation of a so-called "skeleton model." As a method of detecting the feature points P2, well-known various methods can be used, and a detailed explanation of the method will be omitted.

The inclination angle detecting unit 33 generates a skeleton model for the driver by using the multiple feature points P2 detected by the skeletal frame feature point detecting unit 32. The inclination angle detecting unit 33 detects inclination angles θ2 of the driver's shoulders, inclination angles θ3 of the driver's arms, and inclination angles θ4 of the driver's head by using the generated skeleton model. As a method of detecting the inclination angles θ2, θ3, and θ4, well-known various methods can be used, and a detailed explanation of the method will be omitted.

The inclination angles θ2, θ3, and θ4 are detected with respect to, for example, a state in which the driver's face is directed toward the front of the vehicle 1, the back of the driver's head is in contact with the headrest of the driver's seat, the driver's back is in contact with the backrest of the driver's seat, the driver is holding the steering wheel of the vehicle 1 with both hands, and the steering angle of the vehicle 1 is approximately 0 degrees (in other words, the vehicle 1 is substantially going straight). Because a concrete example of the inclination angles θ4 is the same as that of the inclination angles θ1, a detailed explanation of the concrete example will be omitted.

Figure 5:
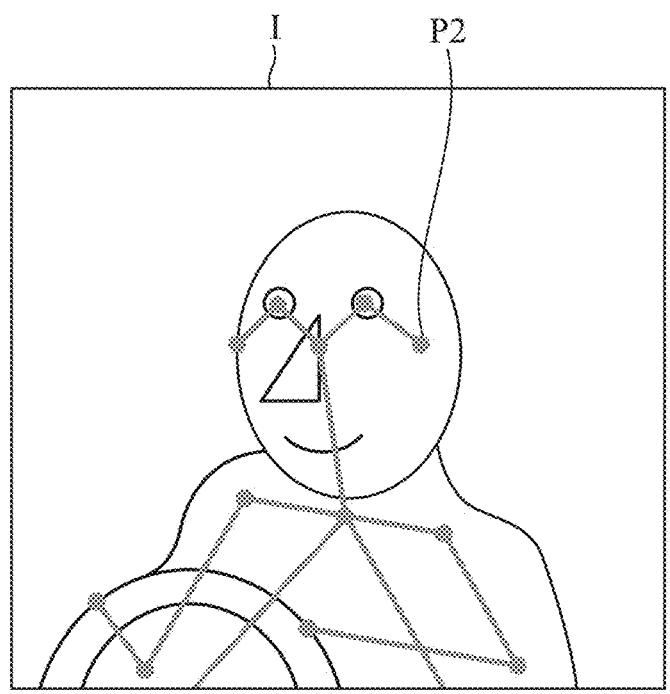
FIG. 5 is an explanatory drawing showing an example of multiple feature points and a skeleton model of a driver.

FIG. 5 shows an example of the multiple feature points P2 and the skeleton model for the driver. In the example shown in FIG. 5, 12 feature points P2 are detected and a skeleton model based on a so-called "stick model" is generated.

A moveless state determining unit 13 determines whether or not the driver is in a state in which there is no movement of the driver (referred to as a "moveless state" hereafter) by using a result of the image recognition processing by the image recognition processing unit 12. Concrete examples of a determining method used by the moveless state determining unit 13 will be mentioned later.

An abnormal state determining unit 14 determines whether or not the driver is in an abnormal state due to decrease in the degree of awakening by using a result of the determination by the moveless state determining unit 13. Hereafter, an abnormal state due to decrease in the degree of awakening is simply referred to as an "abnormal state."

More specifically, the abnormal state determining unit 14 calculates the duration T of the moveless state by using the determination result provided by the moveless state determining unit 13. The abnormal state determining unit 14 compares the calculated duration T with a predetermined reference time Tth. When the duration T exceeds the reference time Tth, the abnormal state determining unit 14 determines that the driver is in an abnormal state.

When the abnormal state determining unit 14 determines that the driver is in an abnormal state, a warning output control unit 15 performs control to output a warning.

Concretely, for example, the warning output control unit 15 performs control to cause a display device 3 to display an image for warning. As an alternative, for example, the warning output control unit 15 performs control to cause a sound output device 4 to output a sound for warning. More specifically, the warning using an image or a sound is intended mainly for the inside of the vehicle.

As an alternative, for example, the warning output control unit 15 performs control to cause a wireless communication device 5 to transmit a signal for warning. The signal is transmitted to a so-called "center" via a wide area network like the Internet. As an alternative, the signal is transmitted to other vehicles traveling in the vicinity of the vehicle 1 via "vehicle-to-vehicle communications." More specifically, the warning using a signal is intended mainly for the outside of the vehicle.

The display device 3 includes, for example, a liquid crystal display (LCD), an organic electro-luminescence display (OLED), or a head-up display (HUD). The sound output device 4 includes, for example, a speaker. The wireless communication device 5 includes, for example, a transmitter for and a receiver for connection with the Internet or a transmitter for and a receiver for vehicle-to-vehicle communications.

The warning output control unit 15 may perform any two or more of the control to cause the display device 3 to display an image for warning, the control to cause the sound output device 4 to output a sound for warning, and the control to cause the wireless communication device 5 to transmit a signal for warning.

A main part of the image recognition processing unit 12 is constituted by the face area detecting unit 21, the face feature point detecting unit 22, the eye opening degree detecting unit 23, the inclination angle detecting unit 24, the facial expression detecting unit 25, the human body area detecting unit 31, the skeletal frame feature point detecting unit 32, and the inclination angle detecting unit 33. A main part of the occupant state determining device 100 is constituted by the image data acquiring unit 11, the image recognition processing unit 12, the moveless state determining unit 13, and the abnormal state determining unit 14. A main part of the warning output control device 200 is constituted by the occupant state determining device 100 and the warning output control unit 15.

Next, the hardware configuration of the main part of the warning output control device 200 will be explained by reference to FIG. 6.

Figure 6A:
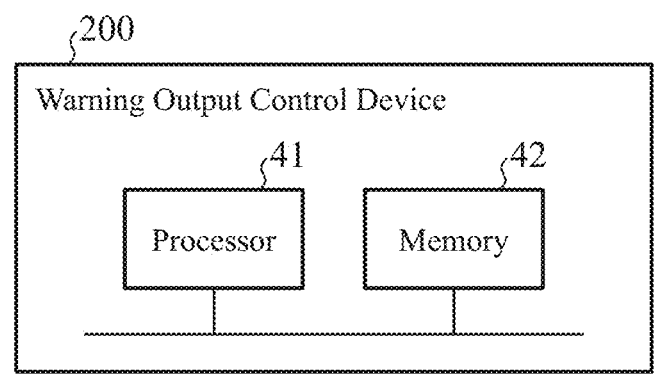
FIG. 6A is a block diagram showing a hardware configuration of the warning output control device according to Embodiment 1.

As shown in FIG. 6A, the warning output control device 200 is constituted by a computer, and the computer has a processor 41 and a memory 42. In the memory 42, a program for causing the computer to function as the image data acquiring unit 11, the image recognition processing unit 12, the moveless state determining unit 13, the abnormal state determining unit 14, and the warning output control unit 15 is stored. The functions of the image data acquiring unit 11, the image recognition processing unit 12, the moveless state determining unit 13, the abnormal state determining unit 14, and the warning output control unit 15 are implemented by the processor 41's reading and executing the program stored in the memory 42.

Figure 6B:
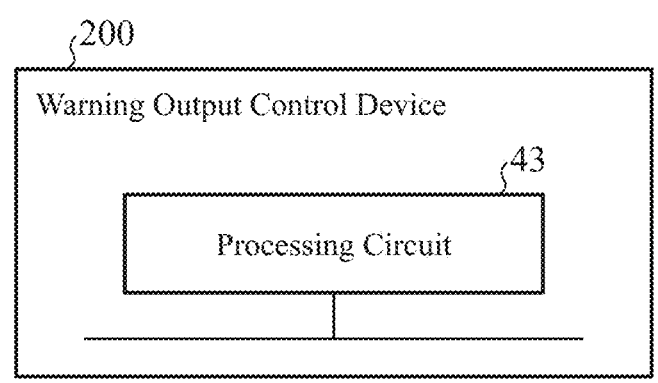
FIG. 6B is a block diagram showing another hardware configuration of the warning output control device according to Embodiment 1.

As an alternative, as shown in FIG. 6B, the warning output control device 200 may have a processing circuit 43. In this case, the functions of the image data acquiring unit 11, the image recognition processing unit 12, the moveless state determining unit 13, the abnormal state determining unit 14, and the warning output control unit 15 may be implemented by the processing circuit 43.

As an alternative, the warning output control device 200 may have the processor 41, the memory 42, and the processing circuit 43. In this case, a part of the functions of the image data acquiring unit 11, the image recognition processing unit 12, the moveless state determining unit 13, the abnormal state determining unit 14, and the warning output control unit 15 may be implemented by the processor 41 and the memory 42, and the remaining part of the functions may be implemented by the processing circuit 43.

As the processor 41, for example, a central processing unit (CPU), a graphics processing unit (GPU), a microprocessor, a microcontroller, or a digital signal processor (DSP) is used.

As the memory 42, for example, a semiconductor memory, a magnetic disc, an optical disc, or a magneto optical disc is used. More concretely, as the memory 42, a random access memory (RAM), a read only memory (ROM), a flash memory, an erasable programmable read only memory (EPROM), an electrically erasable programmable read-only memory (EEPROM), a solid state drive (SSD), a hard disk drive (HDD), a floppy disk (FD), a compact disc (CD), a digital versatile disc (DVD), a magneto-optical (MO), a mini disc (MD), or the like is used.

As the processing circuit 43, for example, an application specific integrated circuit (ASIC), a programmable logic device (PLD), a field-programmable gate array (FPGA), a system-on-a-chip (SoC), or a system large-scale integration (LSI) is used.

Figure 7:
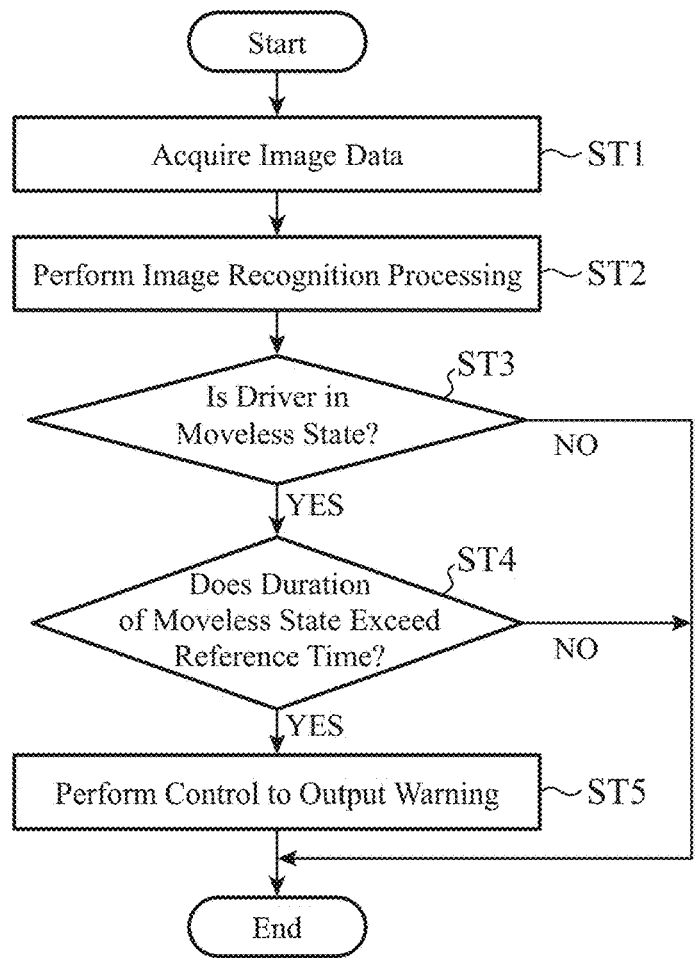
FIG. 7 is a flowchart showing the operation of the warning output control device according to Embodiment 1.

Next, the operation of the warning output control device 200 will be explained by reference to a flowchart of FIG. 7. The warning output control device 200 repeatedly performs the processing shown in FIG. 7 in a state in which, for example, the power is switched on (more concretely, in a state in which the ignition power source of the vehicle 1 is switched on).

First, in step ST1, the image data acquiring unit 11 acquires the image data indicating the captured image I from the camera 2. The image data acquiring unit 11 outputs the acquired image data to the image recognition processing unit 12.

Then, in step ST2, the image recognition processing unit 12 performs the image recognition processing on the captured image I by using the image data outputted by the image data acquiring unit 11. Because a concrete example of the image recognition processing is already explained, an explanation of the concrete example will not be repeated.

Then, in step ST3, the moveless state determining unit 13 determines whether or not the driver is in the moveless state by using a result of the image recognition processing by the image recognition processing unit 12. Concrete examples of the determining method used by the moveless state determining unit 13 will be mentioned later.

When it is determined that the driver is in the moveless state ("YES" in step ST3), the abnormal state determining unit 14, in step ST4, determines whether the duration T of the moveless state exceeds the reference time Tth. This duration T is calculated by the abnormal state determining unit 14.

When it is determined that the duration T of the moveless state exceeds the reference time Tth ("YES" in step ST4), the warning output control unit 15, in step ST5, performs the control to output a warning. Because a concrete example of a method of outputting a warning, the method being used by the warning output control unit 15, is already explained, an explanation of the concrete example will not be repeated.

Next, concrete examples of the determining method used by the moveless state determining unit 13 will be explained by reference to FIGS. 8 to 11.

First Concrete Example of the Determining Method Used by the Moveless State Determining Unit 13

The moveless state determining unit 13 calculates, as to the face areas $A1_n$ and $A1_{n+1}$ in the captured images $I_n$ and $I_{n+1}$ that are two consecutive frames in time (n is an arbitrary integer), the area of a part in which the face areas $A1_n$ and $A1_{n+1}$ overlap each other (referred to as the "overlapping area" hereafter) by using a result of the detection by the face area detecting unit 21. The moveless state determining unit 13 calculates the ratio of the overlapping area to the area of the face area $A1_n$ or $A1_{n+1}$ (referred to as the "overlapping area ratio" hereafter). The moveless state determining unit 13 calculates the amount of movement of the face area A1 on the basis of the overlapping area ratio. For example, the moveless state determining unit 13 calculates the amount of movement in a way that the amount of movement of the face area A1 increases as the overlapping area ratio decreases. When the amount of movement of the face area A1 is less than a predetermined reference quantity, the moveless state determining unit 13 determines that the driver is in the moveless state. The denominator of the overlapping area ratio may be the area of a part corresponding to the sum (more concretely, the logical sum) of the face areas $A1_n$ and $A1_{n+1}$.

Figure 8:
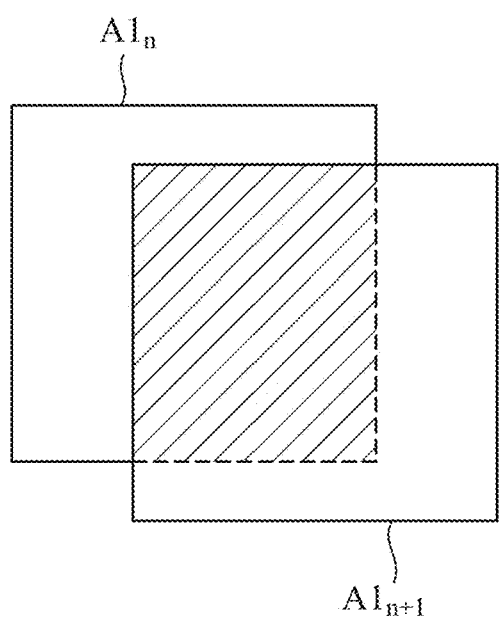
FIG. 8 is an explanatory drawing showing an example of a state in which a face area in an n-th captured image and a face area in an (n+1)-th captured image overlap each other.

FIG. 8 shows an example of a state in which the face area $A1_n$ in the n-th captured image $I_n$ and the face area $A1_{n+1}$ in the (n+1)-th captured image $I_{n+1}$ overlap each other. In the figure, a hatched area shows the part in which the face areas $A1_n$ and $A1_{n+1}$ overlap each other. As mentioned above, the captured images $I_n$ and $I_{n+1}$ correspond to two consecutive frames in time. More specifically, the images $I_n$ and $I_{n+1}$ are captured at mutually different times.

Second Concrete Example of the Determining Method Used by the Moveless State Determining Unit 13

The moveless state determining unit 13 calculates, as to the face areas $A1_n$ and $A1_{n+1}$ in the captured images $I_n$ and $I_{n+1}$ that are two consecutive frames in time (n is an arbitrary integer), the amount of change in the size of the face area $A1_{n+1}$ with respect to the size of the face area $A1_n$ by using the detection result provided by the face area detecting unit 21. This calculated amount of change shows the amount of movement of the head of the driver in a forward or backward direction. When the amount of change in the size of the face area A1 is less than a predetermined reference quantity, the moveless state determining unit 13 determines that the driver is in the moveless state.

Third Concrete Example of the Determining Method Used by the Moveless State Determining Unit 13

The moveless state determining unit 13 calculates the amount of movement of the center of the face area A1 in each of the images I that are captured for the second and subsequent times within a predetermined time period, with respect to the center of the face area A1 in the captured image I that is captured for the first time within the predetermined time period, by using the detection result provided by the face area detecting unit 21. The moveless state determining unit 13 calculates the amount of movement of the face area A1 within the predetermined time period by adding up the calculated amounts of movement. When the amount of movement of the face area A1 is less than a predetermined reference quantity, the moveless state determining unit 13 determines that the driver is in the moveless state.

Fourth Concrete Example of the Determining Method Used by the Moveless State Determining Unit 13

The moveless state determining unit 13 determines whether or not an inclination angle θ1 of the driver's head is equal to or greater than a predetermined reference angle by using a result of the detection by the inclination angle detecting unit 24. The moveless state determining unit 13 determines whether or not the amount of movement of the face area A1 is less than a reference quantity by using the same method as that in the first or third concrete example. When the inclination angle θ1 is equal to or greater than the reference angle and the amount of movement of the face area A1 is less than the reference quantity, the moveless state determining unit 13 determines that the driver is in the moveless state.

Fifth Concrete Example of the Determining Method Used by the Moveless State Determining Unit 13

The moveless state determining unit 13 determines whether or not an inclination angle θ1 of the driver's head is equal to or greater than a predetermined reference angle by using the detection result provided by the inclination angle detecting unit 24. The moveless state determining unit 13 determines whether or not the amount of change in the size of the face area A1 is less than a reference quantity by using the same method as that in the second concrete example. When the inclination angle θ1 is equal to or greater than the reference angle and the amount of change in the size of the face area A1 is less than the reference quantity, the moveless state determining unit 13 determines that the driver is in the moveless state.

Sixth Concrete Example of the Determining Method Used by the Moveless State Determining Unit 13

In general, human eyeblinks are classified into three types. More specifically, they are a "periodic eyeblink" that is performed unconsciously, a "reflexive eyeblink" that is performed when light comes into eyes, and a "spontaneous eyeblink" that is performed spontaneously. In a state in which a human being is awake, a periodic eyeblink is performed at approximately fixed time intervals (i.e., with an approximately fixed frequency).

Accordingly, the moveless state determining unit 13 calculates the frequency of the driver's eyeblinks by using a result of the detection by the eye opening degree detecting unit 23. When the calculated frequency is less than a predetermined threshold, the moveless state determining unit 13 determines that the driver is in the moveless state.

Seventh Concrete Example of the Determining Method Used by the Moveless State Determining Unit 13

The moveless state determining unit 13 calculates so-called "PERCLOS" by using the detection result provided by the eye opening degree detecting unit 23. PERCLOS shows the ratio of time periods $T_{CLOSE}(s)$ during each of which the driver's eyes are closed to a predetermined time period (a so-called "window size") $T_{WINDOW}$. Therefore, the following equation (1) is used for the calculation of PERCLOS.

$$PERCLOS = \Sigma(T_{CLOSE}(s))/T_{WINDOW} \qquad (1)$$

Figure 9:
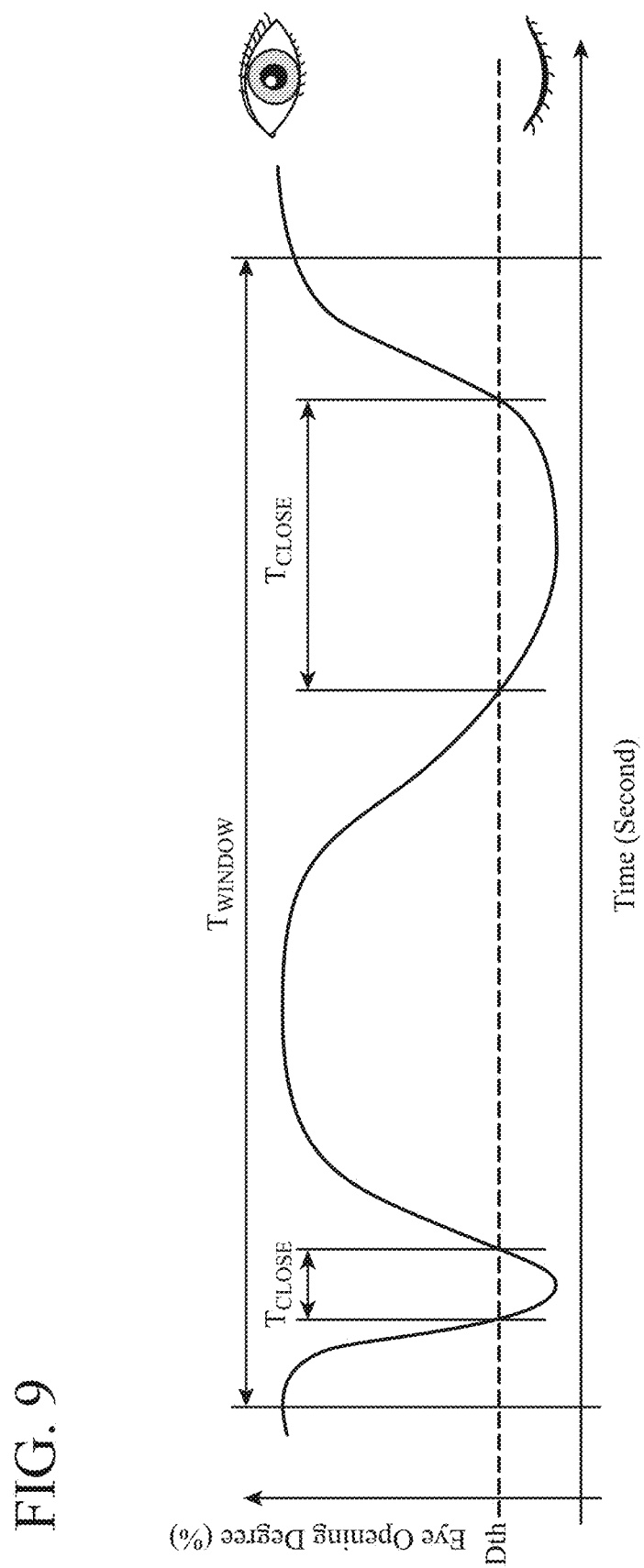
FIG. 9 is an explanatory drawing showing an example of PERCLOS.

FIG. 9 shows an example of PERCLOS. In the figure, Dth is a threshold that is an object to be compared with the eye opening degree D, and is used for the determination of whether the driver is either in a state in which the driver's eyes are open or in a state in which the driver's eyes are closed. The moveless state determining unit 13 calculates, for example, each of $T_{CLOSE}(s)$ by using the predetermined threshold Dth and calculates $\Sigma(T_{CLOSE}(s))$ that is the sum total of these $T_{CLOSE}(s)$, thereby calculating PERCLOS.

The moveless state determining unit 13 calculates PERCLOS for each predetermined time period (i.e., each $T_{WINDOW}$), and calculates the amount of change in these PERCLOS(s). When the amount of change in PERCLOS(s) is less than a predetermined reference quantity, the moveless state determining unit 13 determines that the driver is in the moveless state.

Eighth Concrete Example of the Determining Method Used by the Moveless State Determining Unit 13

The moveless state determining unit 13 acquires information showing the position coordinates of the centers of the face areas $A1_0$ to $A1_{n-1}$ in the captured images $I_0$ to $I_{n-1}$ of n frames (more concretely, the x coordinates $x_0$ to $x_{n-1}$ and the y coordinates $y_0$ to $y_{n-1}$) from the face area detecting unit 21 (n is an integer equal to or greater than 2). The images $I_0$ to $I_{n-1}$ are captured within a predetermined time period (e.g., A+α seconds) starting from a time t1 when a predetermined condition (referred to as a "calibration condition" hereafter) is established. When the image capturing frame rate of the camera 2 is expressed by frame_rate, the relation between n and A is shown by the following equation (2).

$$n = A * \text{frame\_rate} \quad (2)$$

Figures 10A, 10B, 10C:
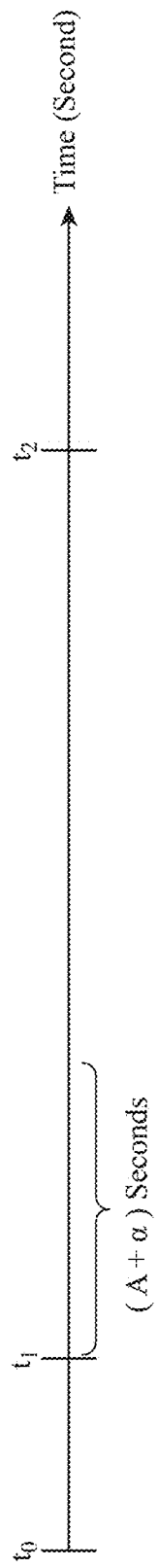
FIG. 10A is an explanatory drawing showing an example of a predetermined time period associated with a reference histogram.
FIG. 10B is an explanatory drawing showing an example of the x and y coordinates of the center of a face area associated with the reference histogram.
FIG. 10C is an explanatory drawing showing an example of the reference histogram.

FIG. 10A shows an example of the predetermined time period (i.e., A+α seconds). FIG. 10B shows an example of the x coordinates $x_0$ to $x_{n-1}$ and the y coordinates $y_0$ to $y_{n-1}$ of the centers of the face areas $A1_0$ to $A1_{n-1}$.

The moveless state determining unit 13 sets up multiple bins in one-to-one correspondence with multiple areas which are spaced at predetermined intervals (e.g., at intervals of B pixels) and into which either the whole of each captured image I or a part of each captured image I (e.g., a part having a greater probability of including the face area A1 in the captured image I than other parts) is divided. The moveless state determining unit 13 generates a histogram in which, as to the n face areas $A1_0$ to $A1_{n-1}$, the number of centers of face areas A1, the centers being included in each bin, is counted. Hereafter, this histogram is referred to as the "reference histogram." FIG. 10C shows an example of the reference histogram.

After that, the moveless state determining unit 13 acquires information indicating the position coordinates of the centers of the face areas $A1_0$ to $A1_{m-1}$ in the captured images $I_0$ to $I_{m-1}$ of m frames (more concretely, the x coordinates $x_0$ to $x_{m-1}$ and the y coordinates $y_0$ to $y_{m-1}$) from the face area detecting unit 21 (m is an integer equal to or greater than 2). The images $I_0$ to $I_{m-1}$ are captured within a predetermined time period (e.g., C seconds) ending at a time t2 when the image $I_{m-1}$ is captured. When the image capturing frame rate of the camera 2 is expressed by frame_rate, the relation between m and C is shown by the following equation (3).

$$m = C * \text{frame\_rate} \quad (3)$$

FIG. 11A shows an example of the predetermined time period (i.e., C seconds). FIG. 11B shows an example of the x coordinates $x_0$ to $x_{m-1}$ and the y coordinates $y_0$ to $y_{m-1}$ of the centers of the face areas $A1_0$ to $A1_{m-1}$.

The moveless state determining unit 13 sets up multiple bins which are similar to those for the reference histogram. The moveless state determining unit 13 generates a histogram in which, as to the m face areas $A1_0$ to $A1_{m-1}$, the number of centers of face areas A1, the centers being included in each bin, is counted. Hereafter, this histogram is referred to as the "histogram for comparison." FIG. 11C shows an example of the histogram for comparison.

The moveless state determining unit 13 compares the value of each bin in the histogram for comparison with the value of the corresponding bin in the reference histogram. As a result, the moveless state determining unit 13 determines the degree of change in the histogram for comparison with respect to the reference histogram. Concretely, for example, the moveless state determining unit 13 determines either the degree of change in the distribution of values in the histogram or presence or absence of change in the position of a bin corresponding to a maximum. As a result, the moveless state determining unit 13 determines presence or absence of change in the driver's face. When it is determined that there is no change in the driver's face, the moveless state determining unit 13 determines that the driver is in the moveless state.

The histogram for comparison may be generated repeatedly at predetermined time intervals after the reference histogram is generated (more specifically, the histogram for comparison may be updated at the predetermined time intervals). Every time the histogram for comparison is generated (more specifically, every time the histogram for comparison is updated), the moveless state determining unit 13 may compare the value of each bin in the newest histogram for comparison with the value of the corresponding bin in the reference histogram.

Ninth Concrete Example of the Determining Method Used by the Moveless State Determining Unit 13

Generally, in a state in which a human being is awake, his or her facial expression changes at approximately fixed time intervals (i.e., with an approximately fixed frequency) depending on the ambient environment, the content of conversation, or the like. In contrast with this, no change in the facial expression occurs in a state in which the degree of awakening decreases. More concretely, a facial expression in which the corners of the mouth are lowered is maintained because of relaxation of mimic muscles.

Accordingly, the moveless state determining unit 13 determines presence or absence of change in the driver's facial expression by using a result of the detection by the facial expression detecting unit 25. When determining that there is no change in the facial expression, the moveless state determining unit 13 determines that the driver is in the moveless state.

Tenth Concrete Example of the Determining Method Used by the Moveless State Determining Unit 13

The moveless state determining unit 13 determines presence or absence of a change in the inclination angles θ2 (i.e., presence or absence of a movement of the driver's shoulder) by using a result of the detection by the inclination angle detecting unit 33. Further, the moveless state determining unit 13 determines presence or absence of a change in the inclination angles θ3 (i.e., presence or absence of a movement of the driver's arm). Further, the moveless state determining unit 13 determines presence or absence of a change in the inclination angles θ4 (i.e., presence or absence of a movement of the driver's head).

The moveless state determining unit 13 determines whether or not the driver is in the moveless state on the basis of results of the determination of presence or absence of these movements. For example, when there are no movements of the driver's shoulders, there are no movements of the driver's arms, and there is no movement of the driver's head, the moveless state determining unit 13 determines that the driver is in the moveless state.

The moveless state determining unit 13 may execute any one of the first to tenth concrete examples or any two or more of the first to tenth concrete examples. In the case of executing any two or more of the first to tenth concrete examples, when it is determined, by using a predetermined number of methods out of the two or more methods, that the driver is in the moveless state, the moveless state determining unit 13 may output a determination result indicating that the driver is in the moveless state to the abnormal state determining unit 14. As an alternative, in this case, the moveless state determining unit 13 may perform weighting on determination results provided by the methods, thereby outputting a final determination result to the abnormal state determining unit 14.

As mentioned above, the occupant state determining device 100 of Embodiment 1 determines whether or not the driver is in the moveless state and determines whether or not the driver is in an abnormal state on the basis of the duration T of the moveless state. Further, the methods of determining whether or not the driver is in the moveless state include methods not using a result of the detection of the eye opening degree D (the first, second, third, fourth, fifth, eighth, ninth, and tenth concrete examples). Therefore, an abnormal state including a microsleep state with eyes open can be determined, and an abnormal state can be determined regardless of whether or not the driver is in a state in which the eye opening degree D is not detected normally.

Further, any of the methods of determining whether or not the driver is in the moveless state (the first to tenth concrete examples) uses the image I captured by the camera 2. More specifically, expensive devices such as living body sensors, are unnecessary. Therefore, the whole of a system including the warning output control device 200 can be implemented at a low cost.

The abnormal state determining unit 14 may acquire information indicating a so-called "autonomous driving level" from an electronic control unit (ECU) for autonomous driving control disposed in the vehicle 1. The autonomous driving level is shown by a value ranging from 0 to 5, and the level 0 shows that the vehicle 1 is traveling while being driven manually. The abnormal state determining unit 14 may set the reference time Tth to a value that differs depending on the autonomous driving level of the vehicle 1 by using the acquired information. For example, when the autonomous driving level is 2 or less, the abnormal state determining unit 14 may set the reference time Tth to a value smaller compared with that in the case in which the autonomous driving level is 3 or more. As a result, the determination of an abnormal state on the basis of a proper reference time Tth can be implemented in accordance with the autonomous driving level of the vehicle 1.

Further, when performing the process of detecting the eye opening degree D, the eye opening degree detecting unit 23 may output information indicating the success or failure of the detection to the moveless state determining unit 13. By using the information outputted by the eye opening degree detecting unit 23, when the eye opening degree detecting unit 23 has succeeded in the detection of the eye opening degree D, the moveless state determining unit 13 may determine whether or not the driver is in the moveless state by means of a method using a result of the detection of the eye opening degree D (at least one of the sixth and seventh concrete examples), whereas when the eye opening degree detecting unit 23 has failed in the detection of the eye opening degree D, the moveless state determining unit 13 may determine whether or not the driver is in the moveless state by means of a method not using a result of the detection of the eye opening degree D (at least one of the first, second, third, fourth, fifth, eighth, ninth, and tenth concrete examples). As a result, the determination of the moveless state using a proper method can be implemented in accordance with the success or failure of the detection of the eye opening degree D.

Further, when having succeeded in the detection of the eye opening degree D, the eye opening degree detecting unit 23 may output information indicating the reliability of the result of the detection to the abnormal state determining unit 14. The abnormal state determining unit 14 may set the reference time Tth to a value that differs depending on the reliability of the result of the detection of the eye opening degree D by using the information outputted by the eye opening degree detecting unit 23. For example, when the reliability is less than a predetermined threshold, the abnormal state determining unit 14 may set the reference time Tth to a value smaller compared with that in the case in which the reliability is equal to or greater than the threshold. As a result, the determination of an abnormal state on the basis of a proper reference time Tth can be implemented in accordance with the reliability of the result of the detection of the eye opening degree D.

Further, in a case in which the determining methods used by the moveless state determining unit 13 do not include the fourth and fifth concrete examples, the image recognition processing unit 12 may be configured so as to exclude the inclination angle detecting unit 24 shown in FIG. 2.

Further, in a case in which the determining methods used by the moveless state determining unit 13 do not include the sixth and seventh concrete examples, the image recognition processing unit 12 may be configured so as to exclude the eye opening degree detecting unit 23 shown in FIG. 2.

Further, in a case in which the determining methods used by the moveless state determining unit 13 do not include the ninth concrete example, the image recognition processing unit 12 may be configured so as to exclude the facial expression detecting unit 25 shown in FIG. 2.

Further, in a case in which the determining methods used by the moveless state determining unit 13 do not include the tenth concrete example, the image recognition processing unit 12 may be configured so as to exclude the human body area detecting unit 31, the skeletal frame feature point detecting unit 32, and the inclination angle detecting unit 33 which are shown in FIG. 2.

Further, the warning outputting method used by the warning output control unit 15 is not limited to the above-mentioned concrete example. For example, the warning output control unit 15 may perform control to light the hazard lamp of the vehicle 1 when the abnormal state determining unit 14 determines that the driver is in an abnormal state.

Further, the occupant state determining device 100 can be used not only for the determination of whether or not the driver is in an abnormal state, but also for the determination of whether or not an occupant different from the driver, out of the occupants in the vehicle 1, is in an abnormal state. For example, when the vehicle 1 is traveling based on autonomous driving with level 3 or higher, the occupant state determining device 100 can also be used for the determination of whether or not an occupant sitting in the driver's seat, but not driving the vehicle 1 is in an abnormal state.

As mentioned above, the occupant state determining device 100 of Embodiment 1 includes the image data acquiring unit 11 that acquires image data indicating an image I captured by the camera 2 used for image capturing in the vehicle cabin, the image recognition processing unit 12 that performs the image recognition processing on the captured image I by using the image data, the moveless state determining unit 13 that determines whether or not an occupant is in the moveless state by using a result of the image recognition processing, and the abnormal state determining unit 14 that determines whether or not the occupant is in an abnormal state due to decrease in the degree of awakening by using a result of the determination by the moveless state determining unit 13, and the abnormal state determining unit 14 determines that the occupant is in an abnormal state when the duration T of the moveless state exceeds the reference time Tth. As a result, an abnormal state including a microsleep state with eyes open can be determined, and an abnormal state can be determined regardless of whether or not the occupant is in a state in which the eye opening degree D is not detected normally.

Further, the abnormal state determining unit 14 sets the reference time Tth to a value that differs depending on the autonomous driving level. As a result, the determination of an abnormal state on the basis of a proper reference time Tth can be implemented in accordance with the autonomous driving level of the vehicle 1.

Further, the image recognition processing includes the process of detecting the eye opening degree D of the occupant, and the abnormal state determining unit 14 sets the reference time Tth to a value that differs depending on the reliability of a result of the detection of the eye opening degree D. As a result, the determination of an abnormal state on the basis of a proper reference time Tth can be implemented in accordance with the reliability of the result of the detection of the eye opening degree D.

Further, the image recognition processing includes the process of detecting the eye opening degree D of the occupant, the determining method used by the moveless state determining unit 13 includes a method using a result of the detection of the eye opening degree D and a method not using a result of the detection of the eye opening degree D, and, when the image recognition processing unit 12 has failed in the detection of the eye opening degree D, the moveless state determining unit 13 determines whether or not the occupant is in the moveless state by using the method not using a result of the detection of the eye opening degree D. As a result, the determination of the moveless state using a proper method can be implemented in accordance with the success or failure of the detection of the eye opening degree D.

Further, the image recognition processing includes the process of detecting the face area A1 in the captured image I, and, when either the amount of movement of the face area A1 or the amount of change in the size of the face area A1 is less than the reference quantity, the moveless state determining unit 13 determines that the occupant is in the moveless state. As a result, for example, the first, second, and third concrete examples can be implemented.

Further, the captured image I includes a first image ($I_n$) and a second image ($I_{n+1}$) which are captured at mutually different times by the camera 2, the face area A1 includes a first face area ($A1_n$) in the first captured image ($I_n$) and a second face area ($A1_{n+1}$) in the second captured image ($I_{n+1}$), and the moveless state determining unit 13 calculates the amount of movement on the basis of the ratio of the area of a part in which the first face area ($A1_n$) and the second face area ($A1_{n+1}$) overlap each other to the area of either the first face area ($A1_n$) or the second face area ($A1_{n+1}$). As a result, for example, the first concrete example can be implemented.

Further, the image recognition processing includes the process of detecting an inclination angle $\theta1$ of an occupant's head, and, when the inclination angle $\theta1$ is equal to or greater than the reference angle and either the amount of movement or the amount of change is less than the reference quantity, the moveless state determining unit 13 determines that the occupant is in the moveless state. As a result, for example, the fourth and fifth concrete examples can be implemented.

Further, the image recognition processing includes the process of detecting the eye opening degree D of the occupant, and the moveless state determining unit 13 determines whether or not the occupant is in the moveless state on the basis of a change in the eye opening degree D. As a result, for example, the sixth and seventh concrete examples can be implemented.

Further, the image recognition processing includes the process of detecting the face area A1 in the captured image I, and the moveless state determining unit 13 generates a reference histogram indicating the positions of the centers of the face areas ($A1_0$ to $A1_{n-1}$) in multiple images ($I_0$ to $I_{n-1}$) captured during a predetermined time period and a histogram for comparison indicating the positions of the centers of the face areas ($A1_0$ to $A1_{m-1}$) in multiple images ($I_0$ to $I_{m-1}$) captured during another predetermined time period, and determines whether or not the occupant is in the moveless state by comparing the reference histogram and the histogram for comparison. As a result, for example, the eighth concrete example can be implemented.

Further, the image recognition processing includes the process of detecting the facial expression of an occupant, and the moveless state determining unit 13 determines whether or not the occupant is in the moveless state on the basis of presence or absence of a change in the facial expression. As a result, for example, the ninth concrete example can be implemented.

Further, the image recognition processing includes the process of detecting the inclination angles $\theta2$, $\theta3$, and $\theta4$ of an occupant's shoulders, arms, and head, by using a skeleton model for the occupant, and the moveless state determining unit 13 determines whether or not the occupant is in the moveless state on the basis of presence or absence of a change in the inclination angles $\theta2$, $\theta3$, and $\theta4$. As a result, for example, the tenth concrete example can be implemented.

Further, the warning output control device 200 of Embodiment 1 includes the occupant state determining device 100, and the warning output control unit 15 that performs control to output a warning when the abnormal state determining unit 14 determines that the occupant is in an abnormal state. As a result, when the driver's abnormal state occurs, a warning to that effect can be outputted.

Further, the warning output control unit 15 performs at least one of control to cause the display device 3 to display an image for warning, control to cause the sound output device 4 to output a sound for warning, and control to cause the wireless communication device 5 to transmit a signal for warning. As a result, when the driver's abnormal state occurs, a warning to that effect can be outputted to inside or outside the vehicle.

Further, the occupant state determining method of Embodiment 1 includes: the step ST1 of, by the image data acquiring unit 11, acquiring image data indicating an image I captured by the camera 2 used for image capturing in the vehicle cabin; the step ST2 of, by the image recognition processing unit 12, performing image recognition processing on the captured image I by using the image data; the step ST3 of, by the moveless state determining unit 13, determining whether or not an occupant is in the moveless state by using a result of the image recognition processing; and the step ST4 of, by the abnormal state determining unit 14, determining whether or not the occupant is in an abnormal state due to decrease in the degree of awakening by using a result of the determination by the moveless state determining unit 13, and the abnormal state determining unit 14 determines that the occupant is in an abnormal state when the duration T of the moveless state exceeds the reference time Tth. As a result, an abnormal state including a microsleep state with eyes open can be determined, and an abnormal state can be determined regardless of whether or not the occupant is in a state in which the eye opening degree D is not detected normally.

Embodiment 2

Figure 12:
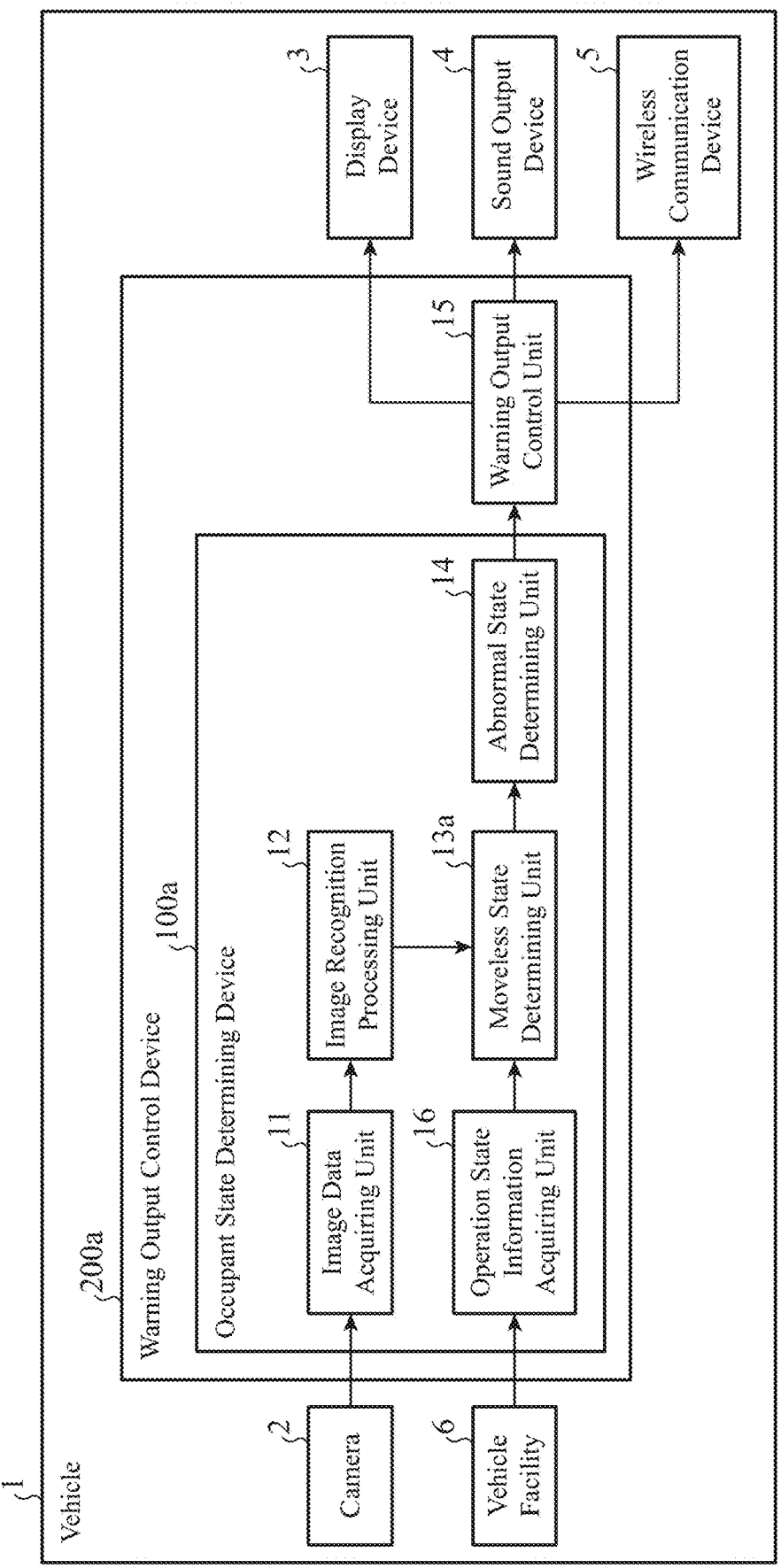
FIG. 12 is a block diagram showing a main part of a warning output control device according to Embodiment 2.

FIG. 12 is a block diagram showing a main part of a warning output control device according to Embodiment 2. Referring to FIG. 12, an occupant state determining device 100a and the warning output control device 200a of Embodiment 2 will be explained. In FIG. 12, the same blocks as those shown in FIG. 1 are denoted by the same reference signs, and an explanation of the blocks will be omitted hereafter.

An operation state information acquiring unit 16 acquires information indicating a state of a driver's operation on a vehicle facility 6 (referred to as "operation state information" hereafter). Concretely, for example, the operation state information acquiring unit 16 acquires the operation state information from the vehicle facility 6 via an in-vehicle network such as a not-illustrated controller area network (CAN).

The vehicle facility 6 is related mainly with the traveling of a vehicle 1. The vehicle facility 6 includes, for example, the steering, the accelerator pedal, the brake pedal, the turn signal, the doors, and the shift lever.

The operation state information acquiring unit 16 outputs the acquired operation state information to a moveless state determining unit 13a.

The moveless state determining unit 13a determines whether or not the driver is in a moveless state by using a result of image recognition processing by an image recognition processing unit 12, and the operation state information outputted by the operation state information acquiring unit 16.

More specifically, the moveless state determining unit 13a determines presence or absence of the driver's operation on the vehicle facility 6 by using the operation state information outputted by the operation state information acquiring unit 16. Further, the moveless state determining unit 13a determines presence or absence of the driver's movement by means of at least one of methods of first to tenth concrete examples, by using the result of the image recognition processing by the image recognition processing unit 12. When determining that there is no driver's operation on the vehicle facility 6 and there is no movement of the driver, the moveless state determining unit 13a determines that the driver is in the moveless state. Because the first to tenth concrete examples are the same as those explained in Embodiment 1, an explanation of the concrete examples will not be repeated.

A main part of the occupant state determining device 100a is constituted by an image data acquiring unit 11, the image recognition processing unit 12, the moveless state determining unit 13a, an abnormal state determining unit 14, and the operation state information acquiring unit 16. A main part of the warning output control device 200a is constituted by the occupant state determining device 100a and a warning output control unit 15.

Further, because the hardware configuration of the main unit of the warning output control device 200a is the same as that explained by reference to FIG. 6 in Embodiment 1, an illustration and an explanation of the hardware configuration will be omitted hereafter. More specifically, the function of the moveless state determining unit 13a may be implemented by either a processor 41 and a memory 42, or a processing circuit 43. Further, the function of the operation state information acquiring unit 16 may be implemented by either the processor 41 and the memory 42, or the processing circuit 43.

Figure 13:
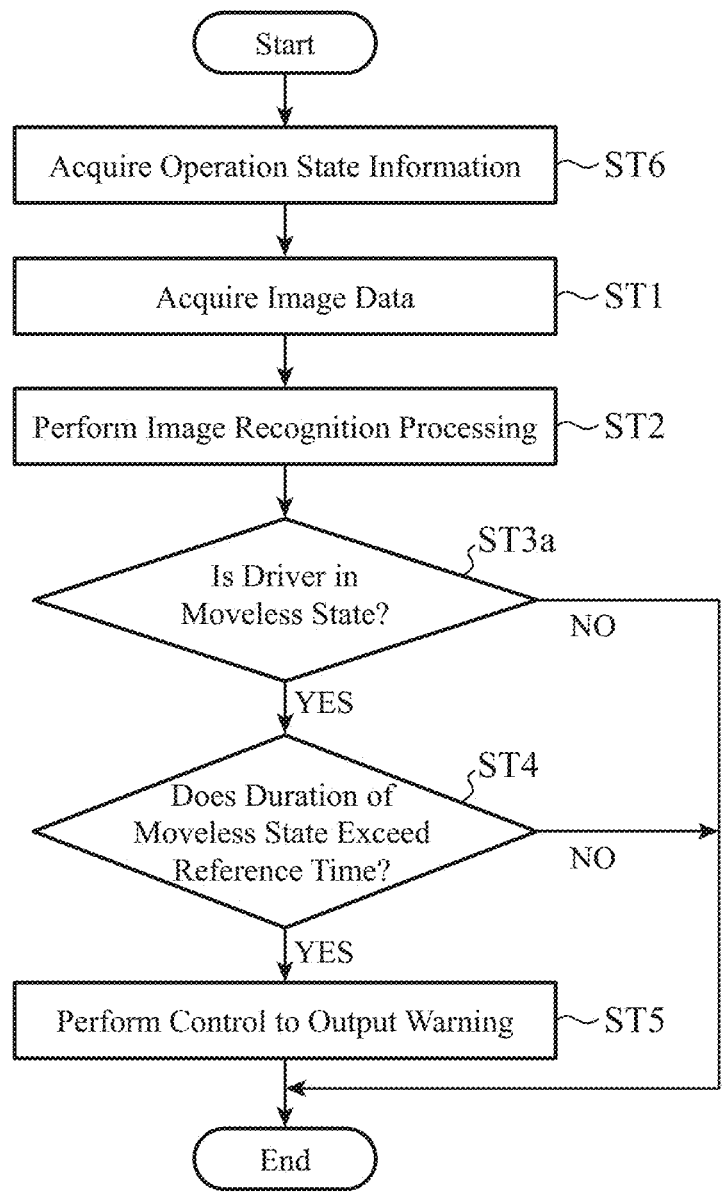
FIG. 13 is a flowchart showing the operation of the warning output control device according to Embodiment 2.

Next, the operation of the warning output control device 200a will be explained by referring to a flowchart of FIG. 13. The warning output control device 200a repeatedly performs the processing shown in FIG. 13 in a state in which, for example, the power is switched on (more concretely, in a state in which the ignition power source of the vehicle 1 is switched on).

First, in step ST6, the operation state information acquiring unit 16 acquires the information about the operation state of the vehicle facility 6. The operation state information acquiring unit 16 outputs the acquired operation state information to the moveless state determining unit 13a.

Then, in step ST1, the image data acquiring unit 11 acquires image data indicating a captured image I from a camera 2. The image data acquiring unit 11 outputs the acquired image data to the image recognition processing unit 12.

Then, in step ST2, the image recognition processing unit 12 performs the image recognition processing on the captured image I by using the image data outputted by the image data acquiring unit 11. Because a concrete example of the image recognition processing is as explained in Embodiment 1, an explanation of the concrete example will not be repeated.

Then, in step ST3a, the moveless state determining unit 13a determines whether or not the driver is in the moveless state by using the result of the image recognition processing by the image recognition processing unit 12, and the operation state information outputted by the operation state information acquiring unit 16. Because a concrete example of a determining method used by the moveless state determining unit 13a is already explained, an explanation of the concrete example will not be repeated.

When it is determined that the driver is in the moveless state ("YES" in step ST3a), the abnormal state determining unit 14, in step ST4, determines whether or not the duration T of the moveless state exceeds a reference time Tth. This duration T is calculated by the abnormal state determining unit 14.

When it is determined that the duration T of the moveless state exceeds the reference time Tth ("YES" in step ST4), the warning output control unit 15, in step ST5, performs control to output a warning. Because a concrete example of a method of outputting a warning, the method being used by the warning output control unit 15, is as explained in Embodiment 1, an explanation of the concrete example will not be repeated.

By thus using the operation state information in addition to the result of the image recognition processing, whether or not the driver is in the moveless state can be determined more correctly.

In a case in which an ECU disposed in the vehicle 1 has an on-board diagnostics (OBD) function, the operation state information acquiring unit 16 may acquire the operation state information outputted by the OBD function.

Further, in a case in which the moveless state determining unit 13*a* implements the eighth concrete example, the moveless state determining unit 13*a* may detect a time t1 when a calibration condition is established by using the operation state information. More specifically, the calibration condition may be one that the driver is not operating the vehicle facility 6. As a result, a reference histogram suitable for comparison with a histogram for comparison (i.e., a reference histogram making it possible to determine whether or not the driver is in the moveless state more correctly by means of the comparison) can be generated.

Further, as the occupant state determining device 100*a*, the same various variants as those explained in Embodiment 1, i.e., the same various variants as those of the occupant state determining device 100 can be employed.

Further, as the warning output control device 200*a*, the same various variants as those explained in Embodiment 1, i.e., the same various variants as those of the warning output control device 200 can be employed.

As mentioned above, the occupant state determining device 100*a* of Embodiment 2 includes the operation state information acquiring unit 16 that acquires operation state information indicating the state of an occupant's operation on the vehicle facility 6, and the moveless state determining unit 13*a* determines whether or not the occupant is in the moveless state by using the result of the image recognition processing, and the operation state information. By using the operation state information in addition to the result of the image recognition processing, whether or not the driver is in the moveless state can be determined more correctly.

It is to be understood that any combination of two or more of the above-mentioned embodiments can be made, various changes can be made in any component according to any one of the above-mentioned embodiments, and any component according to any one of the above-mentioned embodiments can be omitted within the scope of the present disclosure.

INDUSTRIAL APPLICABILITY

The occupant state determining device, the warning output control device, and the occupant state determining method of the present disclosure can be applied to, for example, so-called "driver monitoring systems."

REFERENCE SIGNS LIST

1 vehicle, 2 camera, 3 display device, 4 sound output device, 5 wireless communication device, 6 vehicle facility, 11 image data acquiring unit, 12 image recognition processing unit, 13, 13*a* moveless state determining unit, 14 abnormal state determining unit, 15 warning output control unit, 16 operation state information acquiring unit, 21 face area detecting unit, 22 face feature point detecting unit, 23 eye opening degree detecting unit, 24 inclination angle detecting unit, 25 facial expression detecting unit, 31 human body area detecting unit, 32 skeletal frame feature point detecting unit, 33 inclination angle detecting unit, 41 processor, 42 memory, 43 processing circuit, 100, 100*a* occupant state determining device, and 200, 200*a* warning output control device.

The invention claimed is:

1. An occupant state determining device comprising:
   processing circuitry to
   acquire image data indicating an image captured by a camera used for image capturing in a vehicle cabin;
   perform image recognition processing on the captured image by using the image data;
   determine whether an occupant is in a moveless state by using a result of the image recognition processing; and
   determine whether the occupant is in an abnormal state due to decrease in a degree of awakening by using a result of the determination,
   wherein the image recognition processing includes a process of detecting a face area in the captured image,
   when an amount of movement of the face area or an amount of change in a size of the face area is less than a reference quantity, the processing circuitry determines that the occupant is in the moveless state, and
   the processing circuitry determines that the occupant is in an abnormal state when a duration of the moveless state exceeds a reference time.

2. The occupant state determining device according to claim 1,
   wherein the processing circuitry sets the reference time to a value that differs depending on an autonomous driving level.

3. The occupant state determining device according to claim 1,
   wherein the image recognition processing includes a process of detecting an eye opening degree of the occupant, and
   the processing circuitry sets the reference time to a value that differs depending on reliability of a result of the detection of the eye opening degree.

4. The occupant state determining device according to claim 1,
   wherein the image recognition processing further includes a process of detecting an eye opening degree of the occupant,
   a determining method used by the processing circuitry includes a method using a result of the detection of the eye opening degree and a method not using a result of the detection of the eye opening degree, and
   when the processing circuitry has failed in the detection of the eye opening degree, the processing circuitry determines whether the occupant is in the moveless state by using the method not using a result of the detection of the eye opening degree.

5. The occupant state determining device according to claim 1,
   wherein the captured image includes a first image and a second image which are captured at mutually different timing by the camera,
   the face area includes a first face area in the first captured image and a second face area in the second captured image, and
   the processing circuitry calculates the amount of movement on a basis of a ratio of an area of a part in which the first face area and the second face area overlap each other to an area of either the first face area or the second face area.

6. The occupant state determining device according to claim 1,
wherein the image recognition processing further includes a process of detecting an inclination angle of the occupant's head, and
when the inclination angle is equal to or greater than a reference angle and the amount of movement or the amount of change is less than the reference quantity, the processing circuitry further determines that the occupant is in the moveless state.

7. The occupant state determining device according to claim 1,
wherein the image recognition processing further includes a process of detecting an eye opening degree of the occupant, and
the processing circuitry further determines whether the occupant is in the moveless state on a basis of a change in the eye opening degree.

8. The occupant state determining device according to claim 1,
wherein the image recognition processing further includes a process of detecting a face area in the captured image, and
the processing circuitry further generates a reference histogram indicating a position of a center of a face area in each of multiple images captured during a predetermined time period and a histogram for comparison indicating a position of a center of a face area in each of multiple images captured during another predetermined time period, and determines whether the occupant is in the moveless state by comparing the reference histogram and the histogram for comparison.

9. The occupant state determining device according to claim 1,
wherein the image recognition processing further includes a process of detecting a facial expression of the occupant, and
the processing circuitry further determines whether the occupant is in the moveless state on a basis of presence or absence of a change in the facial expression.

10. The occupant state determining device according to claim 1,
wherein the image recognition processing further includes a process of detecting inclination angles of the occupant's shoulder, arm, and head by using a skeleton model for the occupant, and
the processing circuitry further determines whether the occupant is in the moveless state on a basis of presence or absence of a change in the inclination angles.

11. The occupant state determining device according to claim 1,
wherein the processing circuitry further acquires operation state information indicating a state of the occupant's operation on a vehicle facility,
wherein the processing circuitry determines whether the occupant is in the moveless state by using the result of the image recognition processing and the operation state information.

12. A warning output control device comprising:
the occupant state determining device according to claim 1; and
a warning output controller to perform control to output a warning when it is determined that the occupant is in an abnormal state.

13. The warning output control device according to claim 12, wherein the warning output controller performs at least one of control to cause a display device to display an image for warning, control to cause a sound output device to output a sound for warning, and control to cause a wireless communication device to transmit a signal for warning.

14. An occupant state determining method comprising:
acquiring image data indicating an image captured by a camera used for image capturing in a vehicle cabin;
performing image recognition processing on the captured image by using the image data;
determining whether an occupant is in a moveless state by using a result of the image recognition processing; and
determining whether the occupant is in an abnormal state due to decrease in a degree of awakening by using a result of the determination,
wherein the image recognition processing includes a process of detecting a face area in the captured image, and
when an amount of movement of the face area or an amount of change in a size of the face area is less than a reference quantity, it is determined, by the moveless state determining unit, that the occupant is in the moveless state, and
determining that the occupant is in an abnormal state when a duration of the moveless state exceeds a reference time.

* * * * *